(12) United States Patent
Sen et al.

(10) Patent No.: US 9,176,081 B2
(45) Date of Patent: Nov. 3, 2015

(54) NMR ANALYSIS OF UNCONVENTIONAL RESERVOIR ROCK SAMPLES

(75) Inventors: Pabitra N. Sen, Chapel Hill, NC (US); Gabriela Leu, Cambridge, MA (US); Nicholas Drenzek, Quincy, MA (US); Thomas J. Neville, Broadbeach (AU); Yi-Qiao Song, Newton, MA (US); Ravinath Kausik Kadayam Viswanathan, Somerville, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 1092 days.

(21) Appl. No.: 13/097,404

(22) Filed: Apr. 29, 2011

(65) Prior Publication Data

US 2012/0273193 A1 Nov. 1, 2012

(51) Int. Cl.
*E21B 47/00* (2012.01)
*E21B 31/06* (2006.01)
*G01N 24/08* (2006.01)

(52) U.S. Cl.
CPC .................. *G01N 24/081* (2013.01)

(58) Field of Classification Search
CPC .................................................. G01N 24/081
USPC .............................. 324/303; 166/250.01, 66.5
See application file for complete search history.

(56) References Cited

U.S. PATENT DOCUMENTS 6,326,787 B1 * 12/2001 Cowgill ........................ 324/318
2003/0214287 A1 * 11/2003 Sun et al. ...................... 324/303
2004/0017194 A1 * 1/2004 Saalwachter et al. ......... 324/307
2008/0224696 A1 * 9/2008 Edwards ....................... 324/303
2011/0068788 A1 * 3/2011 Minh ............................ 324/303

FOREIGN PATENT DOCUMENTS

RU 2292541 C1 1/2007
SU 721736 A 3/1980

OTHER PUBLICATIONS

Miknis, F. P., and G. E. Maciel. "C NMR studies of oil shale evaluation and processing." Proc. of 14th Oil Shale Symposium, Colorado Sch. of Mines, Golden, Co (1981). 13.*
Miknis, F. P., Gary E. Maciel, and Victor J. Bartuska. "Cross polarization magic-angle spinning<sup>13</sup>C NMR spectra of oil shales." Organic Geochemistry 1.3 (1979): 169-176.*
Leu, G. et al, "NMR Identification of Fluids and Wettability in Situ in Preserved Cores", Petrophysics, vol. 43, No. 1, Jan.-Feb. 2002, pp. 13-19.

(Continued)

*Primary Examiner* — Melissa Koval
*Assistant Examiner* — Rishi Patel
(74) *Attorney, Agent, or Firm* — Bridget M. Laffey; Jakub Michna; Daniel S. Matthews

(57) ABSTRACT

Systems and methods for magic angle spinning nuclear magnetic resonance analysis of samples from unconventional reservoirs are described. Fast and inexpensive methods are described that can provide reliable information on TOC content, type, and maturity (via the relative abundances of different hydrocarbons, for example) without the need for more extensive sample preparation or destruction. If care is taken during sample recovery and storage, NMR can also yield an estimate of gas-in-place, including detailed typing (e.g. methane vs. ethane). The described MAS NMR analysis is used to determine various properties of unconventional reservoirs, including gas and oil shales, which are useful in evaluating their worth and producibility.

19 Claims, 5 Drawing Sheets

(56) References Cited

OTHER PUBLICATIONS

Chen, Q. et al, "Identification of Endohedral Water in Single-Walled Carbon Nanotubes by 1H NMR", Nano Letters, vol. 8, No. 7, pp. 1902-1905.

Wang, H. et al, "Temperature-Induced Hydrophobic-Hydrophilic Transition Observed by Water Adsorption", Science 3, vol. 322, No. 5898, pp. 80-83.

Gratz, M. et al, "MAS PFG NMR Studies of Mixtures in Porous Materials", AIP Conference Proceedings 1330, 2011, pp. 61-64.

Gutnikov, S. I., "Effect of Aluminum Oxide on Properties of Basalt Glass and Fibers Based on Them", Thesis Abstract for the degree of Candidate of Chemical Sciences, Moscow, 2009, p. 12.

International Search Report & Written Opinion issued in PCT/US2012/033079 on Jul. 12, 2012; 6 pages.

\* cited by examiner

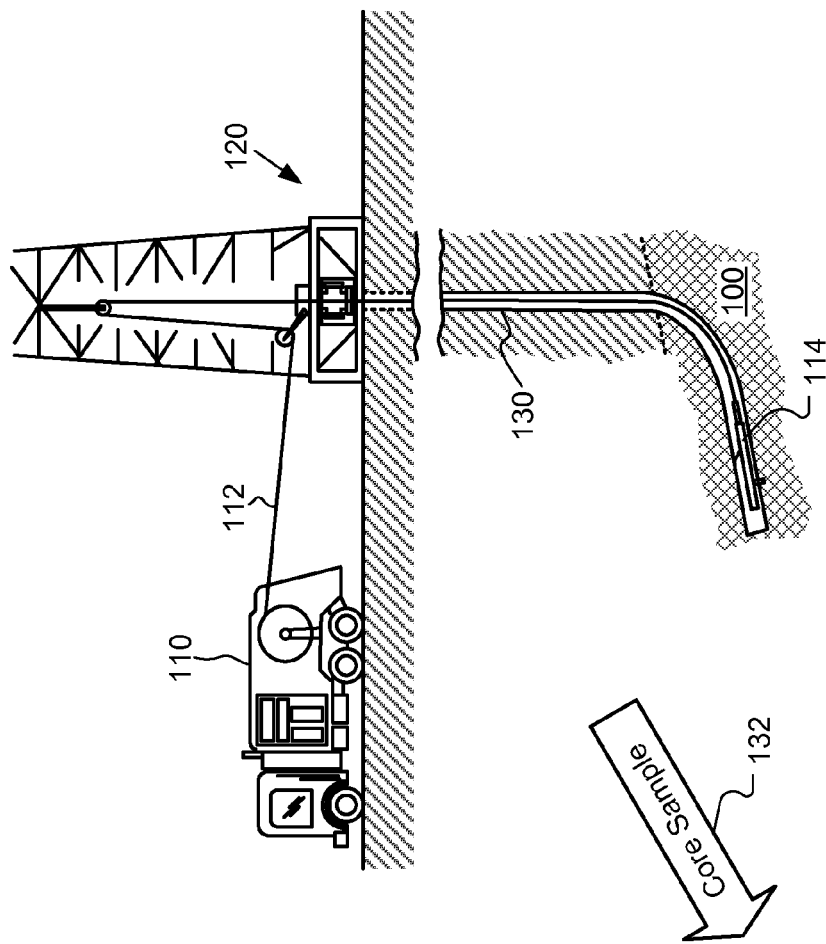
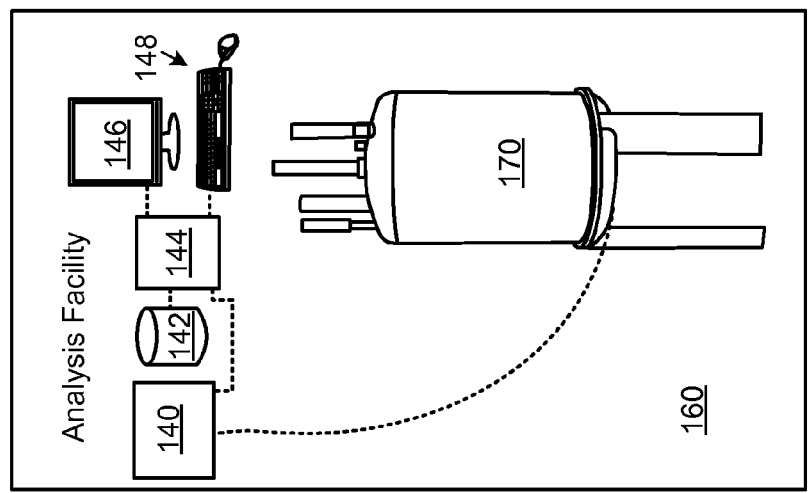
Fig. 1

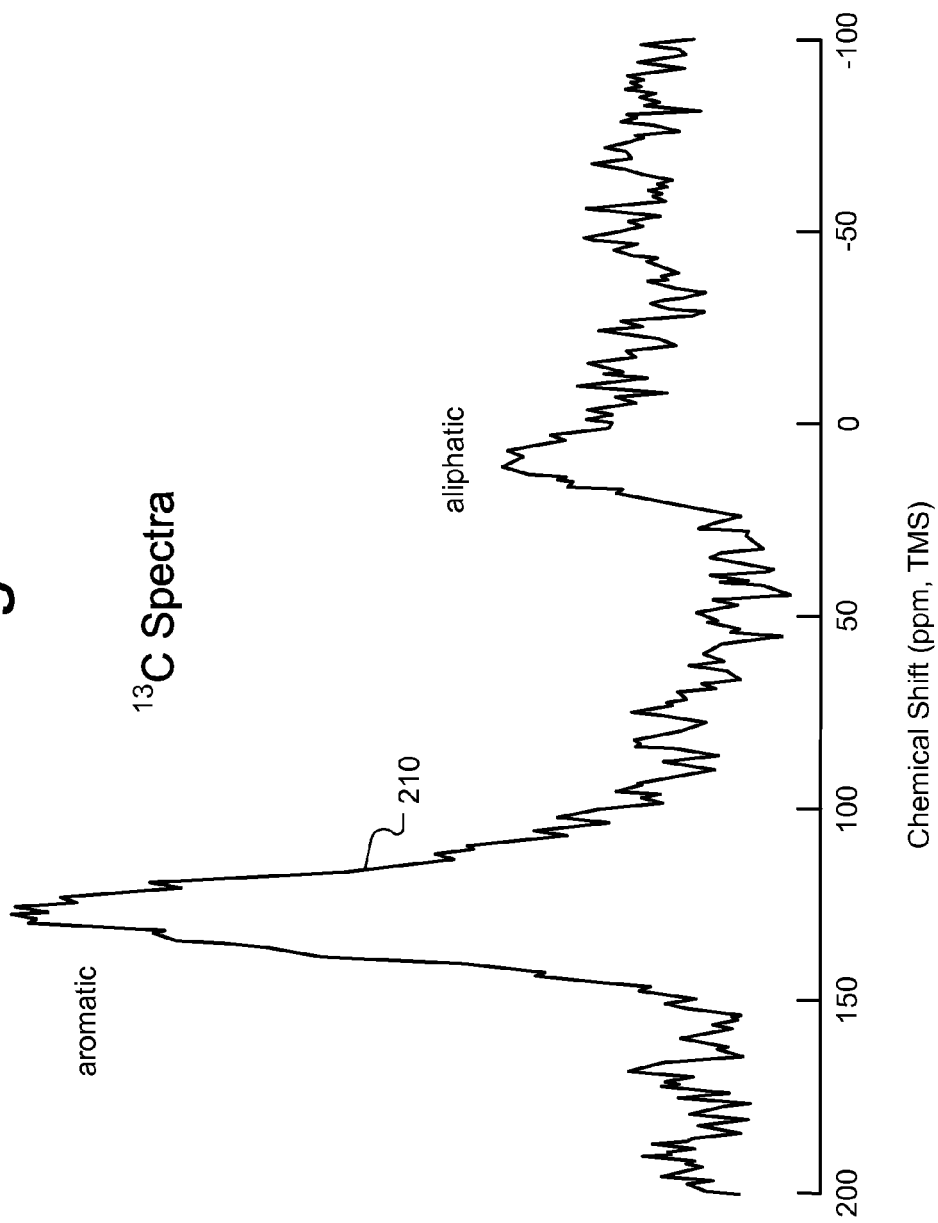

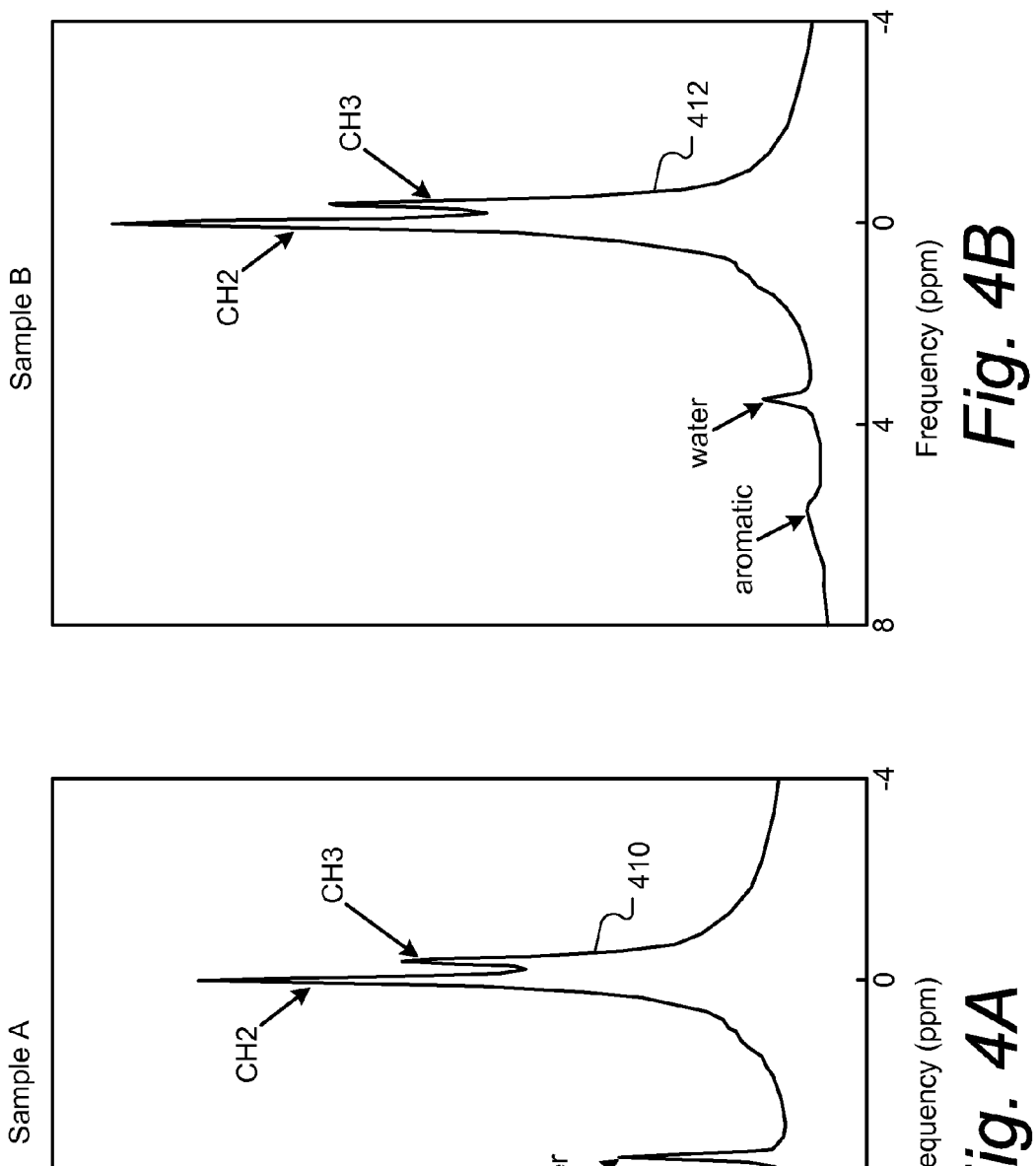

NMR ANALYSIS OF UNCONVENTIONAL RESERVOIR ROCK SAMPLES

FIELD

This patent specification generally relates to Nuclear Magnetic Resonance (NMR) analysis of rock samples from hydrocarbon reservoirs. More particularly, this patent specification relates to the use of Magic Angle Spinning (MAS) NMR analysis techniques for rock samples from unconventional hydrocarbon reservoirs.

BACKGROUND

Due to the advent of horizontal well drilling and the wide application of hydraulic fracturing, production from gas bearing shales is now profitable and consequently represents a significant supply of natural gas in US. However, the mechanism of gas production in association with the hydraulic fracturing is currently not thoroughly understood. For example, only about 10-20% of the injected water is recovered. Furthermore, despite the success of the fracturing technique in gas shale, estimated average gas recovery rates are still quite low at less than 15%.

The key to understanding these phenomena lies in unraveling the complex chemical-physical property relationships of gas shale formations. Gas shales are characteristically composed of various consolidated clay-sized aluminosilicate minerals mixed with varying amounts of calcite, organic matter, methane through butane gas, and water, and exhibit low porosity (several percent) and permeability (millidarcy to nanodarcy levels along and orthogonal to the bedding plane, respectively). Importantly, the abundance, type, and maturity of total organic carbon (TOC), largely in the form of polymeric kerogen, contained within the shale matrix is expected to exert significant control on gas and fracturing water recovery factors. For instance, the micropore network through which fluid flow occurs is often distributed between both hydrophilic mineral and hydrophobic organic phases, with the latter being more ubiquitous at higher maturities. These conditions directly influence the rock wettability and the porosity/permeability, respectively, which consequently affects the overall type and rate of produced fluids from a well.

TOC abundance and type is generally evaluated in the laboratory by pyrolytic or combustion-based techniques. In Rock-Eval pyrolysis, the effluent produced from heating a sample aliquot under an inert atmosphere is monitored in three stages. In the first stage (known as S1), the temperature is kept isothermal at 300° C., releasing the volatile components. The temperature is then ramped to 550° C. in the second stage (S2), resulting in the thermal cracking of the non-volatile organic matter. The evolved matter from these first two stages is quantified with a flame ionization detector (FID). In the third stage (S3), the amount of $CO_2$ produced from 300-390° C. is measured using a thermal conductivity detector (TCD). In this way, the sum of S1+S2+S3 peaks can be used as a crude metric of TOC content, whereas the relative amounts of hydrogen and oxygen in TOC can be approximated using the S2/(S1+S2+S3) and S3/(S1+S2+S3) ratios, respectively. A more accurate measurement of TOC content and type can be derived from combustion-based elemental analysis. This technique involves a tin-catalyzed high temperature combustion of a sample aliquot that has been pre-treated with acid to remove carbonate minerals, subsequent chromatographic separation of the resulting $CO_2$, $N_2$, $H_2O$, and $SO_2$ species, and ultimate TCD quantification to yield the organic carbon, nitrogen, hydrogen, and sulfur content. The oxygen content is similarly obtained under anoxic reactor conditions. TOC maturity, on the other hand, has been traditionally scaled by (a) petrographic observations on whole rock or kerogen isolates, wherein the reflectance properties of organic macerals—primarily vitrinite—are quantified via optical microscopy, (b) the temperature of maximum S2 product generation in Rock-Eval pyrolysis, and (c) biomarker analysis on petroleum extracts, such as the evolution of higher chain length dominated, odd-over-even alkane distributions to shorter chain length, unimodel series as measured by chromatographic and mass spectrometric analyzers.

However, all of these approaches suffer from being time consuming and destructive to the sample.

SUMMARY

According to some embodiments, systems and methods of analyzing rock samples from a subterranean hydrocarbon reservoir are described. The systems and methods include performing magic angle spinning nuclear magnetic resonance spectroscopy on a sample of rock from an unconventional hydrocarbon reservoir; and determining one or more characteristics associated with the sample based at least in part on the spectroscopy. According to some embodiments, the sample of rock from the unconventional hydrocarbon reservoir has unconventional microstructural characteristics, pore sizes of less than about 1 micron, and/or includes significant amounts of kerogen. According to some embodiments, the unconventional hydrocarbon reservoir includes hydrocarbon-bearing shales such as gas shales and oily shales.

The determined characteristics can include geochemical characteristics as well as microstructural characteristics. For example, the determined characteristics can include one or more of the following: total organic carbon content, total organic carbon type, hydrocarbon saturation, water saturation, wettability, intralayer water, interlayer water, hydraulic conductivity, hydraulic porosity, and adsorbed gas content.

According to some embodiments the magic angle spinning nuclear magnetic resonance spectroscopy includes pulse field gradient nuclear magnetic resonance spectroscopy.

As used herein the term "unconventional" reservoir includes reservoirs having an unconventional microstructure, such as having submicron pore size, and/or substantial amounts of primary organic matter such as kerogen. Examples of unconventional reservoirs include hydrocarbon-bearing shales such as gas shales and oily shales.

BRIEF DESCRIPTION OF THE FIGURES

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 1 shows an core sampling tool being deployed in a wellbore and a core analysis facility, according to some embodiments;

FIG. 2 is a plot of a MAS NMR spectrum of organic matter inside a rock, according to some embodiments;

FIGS. 4A-4B shows detail of the MAS spectra shown in FIGS. 3A-3B, according to some embodiments.

DETAILED DESCRIPTION

Figure 3B:
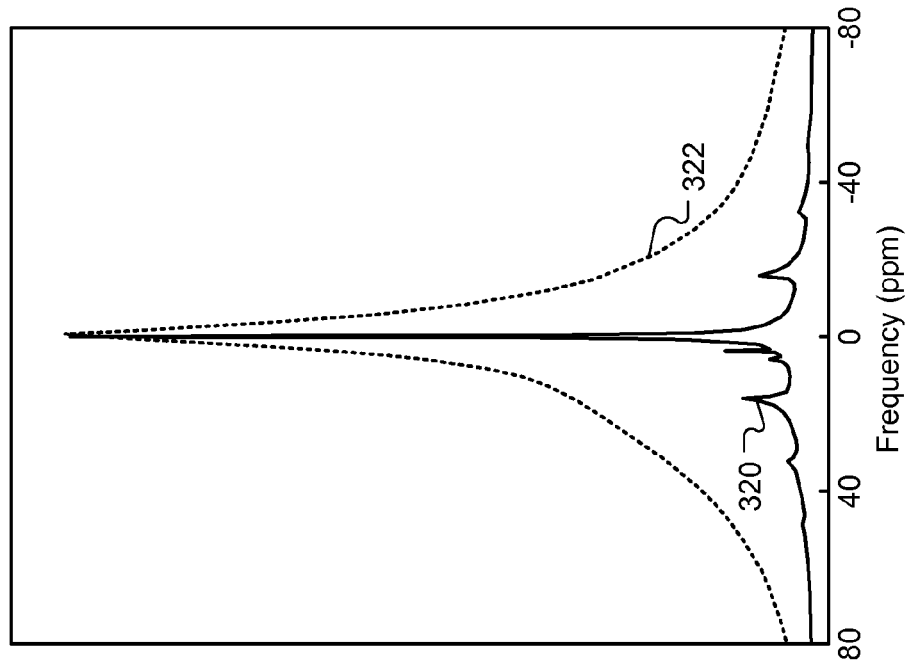
FIGS. 3A-3B are plots showing the static and MAS NMR spectra of two cores saturated with oil and water, according to some embodiments.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicate like elements.

Also, it is noted that individual embodiments may be described as a process that is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

According to some embodiments, a fast and inexpensive method is described that can provide reliable information on TOC content, type, and maturity (via the relative abundances of different hydrocarbons, for example) without the need for more extensive sample preparation or destruction. If care is taken during sample recovery and storage, methane gas NMR can also yield an estimate of gas-in-place, including detailed typing (e.g. methane vs. ethane).

A fast and economic method uses MAS NMR analysis to determine various properties of hydrocarbon-bearing shales that are essential to evaluate their worth and producibility. These measurements can be done with a very small amount of sample—on the order of 1 g. Furthermore, no sample preparation is required and the measurements take only minutes.

Examples of properties that can be determined using MAS NMR analysis include: TOC content; TOC type (aliphatic, aromatic, etc.)—by proton and carbon NMR; hydrocarbon and water saturations; wettability (from comparing MAS NMR relaxation rates of the fluids inside the sample to the relaxation rates of the bulk fluids); intralayer and interlayer water; hydraulic conductivity and porosity (via pore size distribution); and adsorbed gas, including detailed typing (e.g. methane/ethane) when care is taken to retain gas during sampling and storage).

FIG. 1 shows a core sampling tool being deployed in a wellbore and a core analysis facility, according to embodiments. Wireline truck 110 is deploying wireline cable 112 into well 130 via well head 120. Wireline tool 114 is disposed on the end of the cable 112 in an unconventional subterranean formation 100. According to some embodiments, formation 100 is an unconventional reservoir, such as a hydrocarbon-bearing shale reservoir. Tool 114 includes a core sampling tool as shown. Although a wireline core sampling tool is shown, according to other embodiments, other types of core sampling tools are used such as while drilling and/or coiled tubing conveyed tools. Core samples 132 from unconventional rock formation 100 are retrieved at the surface from the tool 114 and transported to an analysis facility 160. Facility 160 includes an MAS NMR machine 170, one or more central processing units 140, storage system 144, communications and input/output modules 140, a user display 146 and a user input system 148. Input/output modules 140 include modules to communicate with and control the MAS NMR machine 170.

Various NMR methods—including imaging, diffusion, and relaxation, have emerged as unique non-invasive probes to study structure and processes in various porous media of biological to geological provenance. NMR spectroscopy is used to identify molecules and their structure. The NMR resonance frequencies depend on the local environment of the individual nuclei and the differences in resonance frequencies (chemical shift) makes it possible to distinguish between nuclei in different chemical environments and thereby identify chemical composition. Since the chemical shift is proportional to the external magnetic field, a strong magnetic field with extremely high homogeneity is desirable for high resolution NMR spectroscopy.

On the other hand, variations in the bulk magnetic susceptibility between the sample constituents, introduce spatially varying local fields which broaden the NMR spectrum. The high applied magnetic fields, which are necessary to separate chemical shifts, make the problem worse because the spread of the inhomogeneous magnetic field (the linewidth) is proportional to the applied magnetic field. Therefore, in systems with large variations in susceptibility, higher magnetic fields do not lead to enhanced spectral resolution. The detrimental effects of these local fields are well documented and lead to a decrease in spectral resolution, non-linearities (distortions) in NMR imaging, and incorrect measurements of molecular diffusion and spin-spin relaxation rates.

The effects of inhomogeneity can be removed by a rotation either in the spin or in the physical space or both. MAS was initially employed for obtaining high resolution NMR spectra of solid samples where the interactions between nuclei produce a broad line that obscures the chemical information. The effects of inhomogeneity can be removed by a rotation either in the spin or in the physical space or both at a 'magic angle' of $\theta_m = \tan^{-1}(\sqrt{2}) = 54.7°$ with respect to the static magnetic field.

In porous or granular media, where the interest is in the fluids in the interstitial space, MAS is employed to average out the range of susceptibility shifts and return the spectra to high resolution. By spinning the sample at frequencies from 1 to 70 kHz, the otherwise broad spectral lines become progressively more narrow, thereby enhancing peak resolution for better identification and analysis of the sample composition.

High-resolution solid state MAS is able to resolve and identify oil and water in rock samples. $^1$H NMR (Proton NMR) under MAS conditions is one such effective method. See, e.g. G. Leu, A. G. Guzman-Garcia, D. G. Cory, and P. N. Sen "NMR Identification of Fluids and Wettability in situ in Preserved Cores" *Petrophysics* 43, 13 (2002), which is incorporated by reference herein. Once oil and water peaks are resolved, their spin dynamics can be investigated individually. Many NMR studies of porous media have established that the spin dynamics ($T_1$, $T_{1\rho}$, $T_2$) are closely related to the interactions of water and oil with pore surfaces. The strong surface effect on spin dynamics indicates wetting while weak effect indicates weak contact with the surface. The wettability of oil and water in rock samples can thus be investigated in detail from such high-resolution spin dynamics studies.

Intralayer and Interlayer Water.

Often times, water and oil in different regions or types of pores in porous media can also be resolved. When looking at an $^1$H NMR spectrum of water in carbon nanotube under MAS at spinning speed of 20 kHz, water inside and outside the nanotubes can be resolved under MAS, whereas no such resolution is possible without MAS. See, Q. Chen, J. L. Herberg, G. Mogilevsky, H. J. Wang, M. Stadermann, J. K. Holt, and Yue Wu "Identification of Endohedral Water in Single-Walled Carbon Nanotubes by $^1$H NMR" *Nano Letters* 8, 1902 (2008), which is incorporated by reference herein. This is an illustration of the principle that one can distinguish two types of water, outside and confined inside nano-size materials. The clays have interlayer separation of the same order of magnitude as the carbon nanotubes and gas shales are typically rich in clays. This method can be used to identify interlayer and intralayer clay water. The relatively high spinning speed of 20 kHz is also important in order to get a clean spectrum where the peak intensities are quantitative (at lower spinning speeds, numerous spinning sidebands can affect spectral resolution and make quantitative analysis difficult).

TOC Type.

The measurement of high-resolution NMR spectra of $^{13}$C requires MAS for the elimination of the broadening due to chemical shift anisotropy. To quantify heavy hydrocarbons in rock, such as bitumen, MAS NMR with $^1$H decoupling or with cross polarization is used. The broadening due to heteronuclear dipole-dipole interaction between $^{13}$C and $^1$H is achieved by irradiating $^1$H with a strong RF field while observing the $^{13}$C nucleus. Because natural abundance of $^{13}$C is only 1%, the nuclear magnetization of $^{13}$C is much lower than that of $^1$H and $T_1$ relaxation time of $^{13}$C is often longer than that of $^1$H, both disadvantages can be alleviated by transfer of magnetization from $^1$H to $^{13}$C with a method called cross polarization. Both $^1$H and $^{13}$C are simultaneously irradiated with resonant RF fields with the amplitudes chosen such that $^1$H and $^{13}$C spins rotate around their individual excitation fields with the same frequency. By this resonant effect transverse $^1$H magnetization can be converted directly into transverse $^{13}$C magnetization.

FIG. 2 is a plot of a MAS NMR spectrum of organic matter inside a rock, according to some embodiments. In particular, plot 210 is a $^{13}$C MAS spectrum (12 kHz spinning rate) of such organic matter in rock where the aromatic and aliphatic components of TOC can be distinguished. Again, higher spinning speed would improve quantitative analysis and afford higher resolution due to better proton decoupling. Finally, MAS NMR under variable temperature can also be analyzed, according to some embodiments. For example, it was recently demonstrated that wetting can also depend on temperature. See, Hai-Jing Wang, Xue-Kui Xi, Alfred Kleinhammes, and Yue Wu "Temperature-Induced Hydrophobic-Hydrophilic Transition Observed by Water Adsorption" Science 322, 80 (2008), which is incorporated by reference herein.

MAS-PFG-NMR.

The advantages of the spectral resolution and the ability to separate the water from the aromatic and aliphatic peaks of the organic content using MAS NMR has been explained herein. We have also shown that the spectroscopic dimension can be used to separate the intra and inter layer water. The organic pores in the shale are generally hydrophobic and thus most of the water resides in the clay and mineral matrix pores. According to some embodiments, a method is provided to separate the different kinds of water by performing MAS-PFG-NMR. In this methodology Pulse Field Gradient (PFG) NMR experiments are carried out while Magic Angle Spinning and thus the diffusion coefficients are obtained along with spectroscopic resolution. This methodology provides for not only all the water being separately visualized in the spectroscopic dimension, but also the different kinds of water separated from each other on the diffusion dimension. This technique has previously been used to spectrally separate various n-alkane mixtures contained within silica gel or zeolite material and to understand the diffusion coefficients of the various components. See, M. Gratz, S. Hertel, M. Wehring, S. Schlayer, F. Stallmach, and P. Galvosas "MAS PFG NMR Studies of Mixtures in Porous Materials", AlP Conf. Proc. 1330, 61 (2011), DOI:10.1063/1.3579178, which is incorporated by reference herein.

Such a similar approach is also useful in separating the whole bitumen from the lighter components in the case of oil bearing shale. This also serves as a suitable way to separate the gas trapped in closed pores from the rest of the organic contributions, since the gas diffusion coefficients are at least an order of magnitude greater for the former relative to the latter.

Hydrocarbon Typing and Wettability.

Figure 3A:
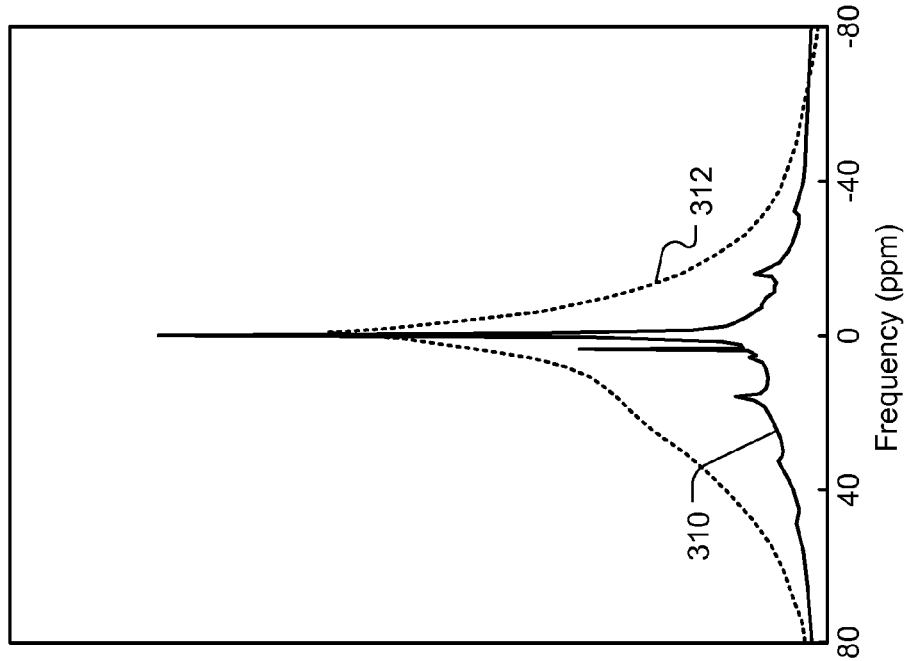

FIGS. 3A-3B are plots showing the NMR spectra of two cores saturated with oil and water, according to some embodiments. FIG. 3A shows the static spectrum 312, and the MAS spectrum 310 spun at 8 kHz for a core Sample A. FIG. 3B shows the static spectrum 322, and the MAS spectrum 320 spun at 8 kHz for a core Sample B. Note that the static spectra 312 and 322 are very broad and featureless and it is not possible to distinguish between the water and oil signals. On the other hand, by the spinning sample at 8 kHz the different fluids present in the pore of the sample are clearly resolved. Spinning sidebands appearing at multiples of the spinning frequency are visible. The spectra were taken at 20° C. and 12 T.

FIGS. 4A-4B shows detail of the MAS spectra shown in FIGS. 3A-3B, according to some embodiments. The spectra 410 and 412 for Samples A and B respectively show in the region of interest, centered in the area where the water and oil peaks are present. The hydrocarbon and water can be clearly identified and their saturations can be determined as they are directly proportional with the areas under the peaks. The NMR relaxation times of water and oil can be measured separately. By spinning the samples at 8 kHz we show that we can distinguish between water and the different types of hydrocarbons present in the sample. The oil has three distinguishable peaks, aliphatics to the right of the water peak and aromatics to the left of the water peak. Thus, MAS offers the opportunity to identify and quantify the water and hydrocarbon present in the sample and to measure their relaxation properties individually.

The fluids which are in direct contact with the rock surface undergo enhanced relaxation because of the presence of paramagnetic ions or magnetic impurities on the rock surface. When a single fluid phase is present in the rock, the relaxation time is dominated by surface relaxation effects. However, when two phases are present, the nonwetting fluid is not affected by surface relaxation because the pore surface is coated by the wetting fluid. Comparing the relaxation of water and oil inside the rock with that of the bulk fluids outside the rock can be used to infer which fluid is wetting the rock.

Figure 5:
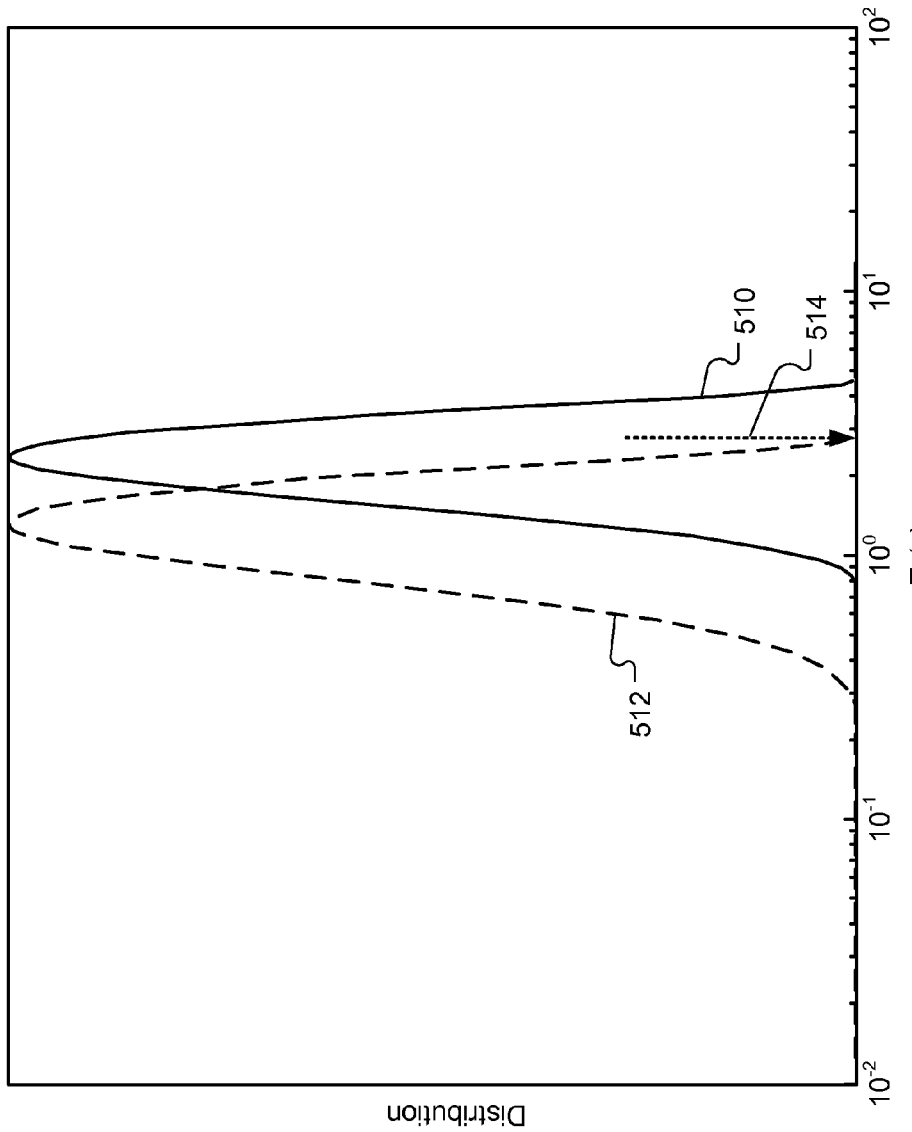
FIG. 5 illustrates the $T_1$ distributions for the water peak in the Sample cores A and B, according to some embodiments.

In the case of the two cores discussed above, the spin-lattice relaxation time, $T_1$, is measured by the inversion-recovery method. With the sample spinning at 8 kHz, a 180° RF pulse inverts all the spins which are then allowed to relax for a fixed recovery time. A final 90° pulse excites the magnetization in the transverse plane after which the signal is collected. FIG. 5 illustrates the $T_1$ distributions for the water peak in the Sample cores A and B, according to some embodiments. Curve 510 shows the $T_1$ distribution for Sample A, and curve 512 for Sample B. The arrow 514 indicates the $T_1$ of bulk water (almost 3 seconds). In this case, the mean $T_1$ for Sample A is closer to the mean $T_1$ of bulk water while for Sample B is significantly shorter. Therefore we infer that for Sample A the water is in poor contact with the pore walls while in Sample B the water relaxes mainly at the pore surface. Thus, Sample A is not water wet while Sample B is mixed or water wet.

When water is the wetting phase, its relaxation times are shortened by surface relaxation and the distribution of the water relaxation times is an indication of the pore size distribution of the pore space occupied by water. In this case, the hydrocarbon relaxation is not affected by the surface interactions and it is determined by its intrinsic composition.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. A method of analyzing rock samples from a subterranean hydrocarbon reservoir comprising:
   performing magic angle spinning nuclear magnetic resonance spectroscopy on a sample of rock from an unconventional hydrocarbon reservoir wherein the magic angle spinning nuclear magnetic resonance spectroscopy includes pulse field gradient nuclear magnetic resonance spectroscopy;
   determining one or more characteristics associated with said sample of rock based at least in part on said magic angle spinning nuclear magnetic resonance spectroscopy; and
   wherein the one or more characteristics include measurements of one or more types selected from a group consisting of: total organic carbon content, total organic carbon type, hydrocarbon saturation, water saturation, wettability, intralayer water, interlayer water, hydraulic conductivity, hydraulic porosity, and gas type.

2. A method according to claim 1 wherein the sample of rock from the unconventional hydrocarbon reservoir has unconventional microstructural characteristics.

3. A method according claim 2 wherein the unconventional microstructural characteristic is pore sizes of less than about 1 micron.

4. A method according to claim 1 wherein the sample of rock from the unconventional hydrocarbon reservoir includes significant amounts of kerogen.

5. A method according to claim 1 wherein the unconventional hydrocarbon reservoir includes hydrocarbon-bearing shales.

6. A method according to claim 5 wherein the unconventional hydrocarbon reservoir includes gas shales.

7. A method according to claim 5 wherein the unconventional hydrocarbon reservoir includes oily shales.

8. A method according to claim 1 wherein the one or more characteristics includes geochemical characteristics.

9. A method according to claim 1 wherein the one or more characteristics includes microstructural characteristics.

10. A system for analyzing rock samples from a subterranean hydrocarbon reservoir comprising a magic angle spinning nuclear magnetic resonance spectroscopy system adapted to perform analysis on a sample of rock from an unconventional hydrocarbon reservoir; wherein the magic angle spinning nuclear magnetic resonance spectroscopy includes pulse field gradient nuclear magnetic resonance spectroscopy, and to determine therefrom one or more characteristics associated with the sample of rock wherein the one or more characteristics include measurements of one or more types selected from a group consisting of: total organic carbon content, total organic carbon type, hydrocarbon saturation, water saturation, wettability, intralayer water, interlayer water, hydraulic conductivity, hydraulic porosity, and gas type.

11. A system according to claim 10 wherein the sample of rock from the unconventional hydrocarbon reservoir has unconventional microstructural characteristics.

12. A system according to claim 11 wherein the unconventional microstructural characteristic is pore sizes of less than about 1 micron.

13. A system according to claim 10 wherein the sample of rock from the unconventional hydrocarbon reservoir includes significant amounts of kerogen.

14. A system according to claim 10 wherein the unconventional hydrocarbon reservoir includes hydrocarbon-bearing shales.

15. A system according to claim 14 wherein the unconventional hydrocarbon reservoir includes gas shales.

16. A system according to claim 14 wherein the unconventional hydrocarbon reservoir includes oily shales.

17. A system according to claim 10 wherein the one or more characteristics includes geochemical characteristics.

18. A system according to claim 10 wherein the one or more characteristics includes microstructural characteristics.

19. The method of claim 1, wherein the sample of rock is a core sample.

* * * * *